United States Patent [19] [11] Patent Number: 5,968,009
Simán [45] Date of Patent: Oct. 19, 1999

[54] DOUBLE LUMEN TUBING DESIGN FOR CATHETER

[75] Inventor: Jaime E. Simán, Santa Ana, Calif.

[73] Assignee: Baxter International Inc., Deerfield, Ill.

[21] Appl. No.: 09/015,049

[22] Filed: Jan. 28, 1998

Related U.S. Application Data

[63] Continuation-in-part of application No. 08/791,079, Jan. 29, 1997, Pat. No. 5,795,326.

[51] Int. Cl.$^6$ .......................................................... A61M 5/00
[52] U.S. Cl. ............................ 604/43; 604/523; 604/534
[58] Field of Search .............................. 604/43, 523, 524, 604/532, 533, 534, 264

[56] References Cited

U.S. PATENT DOCUMENTS

| | | |
|---|---|---|
| 4,568,329 | 2/1986 | Mahurkar . |
| 4,619,643 | 10/1986 | Bai . |
| 4,643,711 | 2/1987 | Bates . |
| 4,682,978 | 7/1987 | Martin . |
| 4,772,268 | 9/1988 | Bates . |
| 4,776,841 | 10/1988 | Catalano . |
| 5,053,023 | 10/1991 | Martin . |
| 5,106,368 | 4/1992 | Uldall et al. . |
| 5,156,592 | 10/1992 | Martin et al. . |
| 5,217,482 | 6/1993 | Keith . |
| 5,364,376 | 11/1994 | Horzewski et al. . |
| 5,380,276 | 1/1995 | Miller et al. . |
| 5,397,302 | 3/1995 | Weaver et al. . |
| 5,425,714 | 6/1995 | Johnson et al. . |
| 5,480,380 | 1/1996 | Martin . |
| 5,554,136 | 9/1996 | Luther . |

FOREIGN PATENT DOCUMENTS

| | | |
|---|---|---|
| 333 308 | 9/1989 | European Pat. Off. . |
| 333308B1 | 9/1989 | European Pat. Off. . |
| 370 158 | 5/1990 | European Pat. Off. . |
| 521 430 | 1/1993 | European Pat. Off. . |
| 521430A1 | 1/1993 | European Pat. Off. . |
| 537 136 | 4/1993 | European Pat. Off. . |
| 05 59 662 | 7/1994 | European Pat. Off. . |
| 495 263 | 3/1996 | European Pat. Off. . |
| 495263B1 | 3/1996 | European Pat. Off. . |
| 40 37 641 | 6/1992 | Germany . |
| WO 89/09633 | 12/1994 | WIPO . |
| WO 94/27666 | 12/1994 | WIPO . |
| WO 96/00100 | 1/1996 | WIPO . |
| WO 96/24399 | 8/1996 | WIPO . |

*Primary Examiner*—John D. Tasko
*Attorney, Agent, or Firm*—Guy L. Cumberbatch; Lena I. Vinitaskaya

[57] ABSTRACT

A double lumen tubing which is adapted for use as a catheter. The tubing accommodates multiple sized guidewires and has increased resistance to kinking. A lumen wall divides the outer tubular wall into the two lumens and has a central arcuate portion shaped to allow insertion of relatively large guidewires through one of the lumens, while still leaving space for smaller guidewires through the other lumen. Resistance to kinking is increased by varying internal diameters or axes of the interior lumen walls to increase the wall thickness of the tubing in selected areas, and by varying the thickness of the wall that divides both lumens in the middle or where the dividing wall meets the outer tubular wall.

21 Claims, 4 Drawing Sheets

DOUBLE LUMEN TUBING DESIGN FOR CATHETER

This application is a continuation-in-part of U.S. application Ser. No. 08/791,079, filed Jan. 29, 1997, now U.S. Pat. No. 5,795,326.

BACKGROUND OF THE INVENTION

1. Field of the Invention

The present invention relates generally to medical devices which are used to provide access into the human body. More particularly, the present invention is directed to double lumen catheters which are used to provide infusion and/or removal of fluids from the body.

2. Description of Related Art

Central venous catheters are relatively long tubular devices which have tapered distal tips which are designed for entry into central veins to provide a dedicated route of fluid infusion into the body. The original venous catheters were single lumen devices which provided the ability to infuse a single liquid into the vein at one time. Multiple lumen catheters have since been developed which allow simultaneous introduction of two or more liquids into the vein. The dual lumen catheter is a common design which has been widely used for a number of years.

Dual lumen catheters include a tubular wall which forms a fluid conduit which typically has a circular cross-section. A single divider or lumen wall is formed inside the tubular wall to divide the circular fluid conduit into two lumens. In many instances, it is desirable that the two lumens have cross-sectional areas which are substantially equal. For example, equal lumen size is desirable in situations where the ability to provide two conduits with maximized fluid delivery rates on both lines is important.

Guidewires are commonly used to insert and locate catheters within the vascular system. The distal end of the guidewire is typically inserted into the vascular system and moved to the desired location for the catheter. The distal end of the catheter is then slipped over the guidewire and the catheter inserted into position as guided by the wire. Once the catheter is in position, the guidewire is withdrawn. It is important that the dual lumen catheter be designed to accommodate the use of guidewires. Some dual lumen catheters have included a separate lumen which is specifically designed to receive the guidewire while others have utilized one or both of the two fluid lumens as a temporary guidewire lumen. An advantage of designing and using one specific fluid lumen to receive the guidewire is that the overall size of the dual lumen catheter is minimized. This reduces the size of the wound made during insertion of the catheter into the body and reduces the wound healing time.

An important consideration in designing dual lumen catheters is to make the catheter as kink resistant as possible. In the past, kinking of the catheter during insertion into the body has been a significant problem. Accordingly, it is desirable that the cross-sectional configuration and other design features be chosen to maximize resistance to catheter kinking.

The currently available dual lumen catheters are adequate for their intended purpose. However, there is a continuing need to develop better dual lumen designs. For example, there is a continuing need to provide dual lumen catheters where the cross-sectional areas, i.e. size, of the lumens is kept substantially similar while at the same time the kink resistance and guidewire compatibility of the dual lumen catheter are improved.

SUMMARY OF THE INVENTION

In accordance with one embodiment of the present invention, a dual lumen tubing is provided which is specifically designed for use as a catheter wherein the cross-sectional areas of the two lumens are substantially equal. The cross-sectional design of the dual lumen catheter is such that the size of the lumens are kept the same while the ability of the catheter to receive multiple size guidewires is increased. In addition, the catheter cross-sectional design provides for increased kink resistance. In an alternative embodiment, the increased ability of the catheter to receive multiple size guidewires and increased kink resistance are provided in a dual lumen tubing with two lumens having cross-sections which are unequal in size yet both suitable for receiving guidewires or for passing fluid or other instruments.

The present invention provides a double lumen tubing adapted for use as a catheter, comprising a tubular wall having an exterior surface located about a longitudinal central axis and an interior surface. The interior surface cross-section is defined by a circular first lumen portion located along a first lumen radius about a first longitudinal axis and a circular second lumen portion located along a second lumen radius about a second longitudinal axis. The tubing further includes a lumen wall extending longitudinally parallel to the central axis and extending transversely across the tubular conduit between spaced locations on the interior surface. The lumen wall comprises a central arcuate portion and has a first surface which, with the first lumen portion of the interior surface, borders a first lumen, the first lumen having a cross-sectional area. The lumen wall further comprises a second surface opposite the first surface which, with the second lumen portion of the interior surface, borders a second lumen, the second lumen having a cross-sectional area. The first surface of the lumen wall has a central convex arcuate portion and adjacent wing portions extending in opposite directions to the tubular wall, while the second surface of the lumen wall has a central concave arcuate portion and adjacent wing portions extending in opposite directions to the tubular wall. The concave arcuate portion is in the shape of a circular arc which has a radius that is from 50 to 90 percent of the radius of the second lumen portion of the interior surface, and a circular primary guidewire region is formed in the second lumen bordered on one side by the concave arcuate portion and on the other side by the second lumen portion, the primary guidewire region having a radius of from 50 to 70 percent of the radius of the second lumen portion.

In one specific embodiment, the lumens are substantially equal in cross-section and the concave central arcuate portion is in the shape of a circular arc which has a radius that is 50 to 60 percent of the radius of the second lumen portion of the interior surface. The concave central arcuate portion, when combined with the second lumen portion forms a circular guidewire region in the second lumen which has a radius which is from 50 to 60 percent of the radius of the second lumen portion. This particular shape of the lumen wall allows the use of guidewires which are relatively large with respect to the overall cross-sectional area of the tubular conduit defined by the tubular wall, while at the same time the cross-sectional areas of the first and second lumens may be substantially equal.

As a feature of the present invention, the exterior surface of the tubular wall may have a circular cross-section which is concentrically located about the interior surface of the tubular wall. In these situations, the kink resistance of the tubing is increased by making the radius of the first lumen portion of the interior wall less than the radius of the second lumen portion to thereby provide a tubular wall having varying thicknesses wherein the thickness of the tubular wall adjacent to the first lumen is greater than the thickness of the tubular wall adjacent to the second lumen. The arcuate lumen wall design may result in a larger circumferential section of the tubular wall being unsupported in the first lumen portion as opposed to the second lumen portion. Accordingly, the increased thickness in lumen wall along the first lumen portion provides increased kink resistance which is specifically applicable to the arcuate lumen wall feature of applicants' invention.

The particular positioning and shape of the lumen wall which in accordance with the present invention provides a dual lumen tubing which is particularly well-suited for use as a dual lumen catheter that has relatively large guidewire compatibility and kink resistance.

The above discussed and many other features and attendant advantages of the present invention will become better understood by reference to the following detailed description when taken in conjunction with the accompanying drawings.

DETAILED DESCRIPTION OF THE PREFERRED EMBODIMENTS

The double lumen tubing in accordance with the present invention is designed for use as a catheter. The tubing can be used in any catheter application and as part of any catheter device where a dual lumen tubing is required having two lumens with substantially the same cross-sectional area. The cross-sectional areas are considered to be substantially equal in accordance with the present invention if the larger of the two areas is no more than approximately 15% larger than the smaller. A first preferred exemplary double lumen tubing in accordance with the present invention is shown generally at 10 in FIG. 1. The double lumen tubing 10 includes a tubular wall 12 and a lumen wall 14. The tubular wall 12 has an exterior surface 16 and an interior surface 18. The interior surface 18 has a circular cross-section located about a longitudinal central axis 20. The interior surface 18 defines a tubular conduit across which the lumen wall 14 extends transversely. The lumen wall 14 also extends parallel to the longitudinal central axis 20. In this preferred embodiment, the exterior surface 16 has a circular cross-section which is concentrically located about the interior surface 18.

Figure 1:
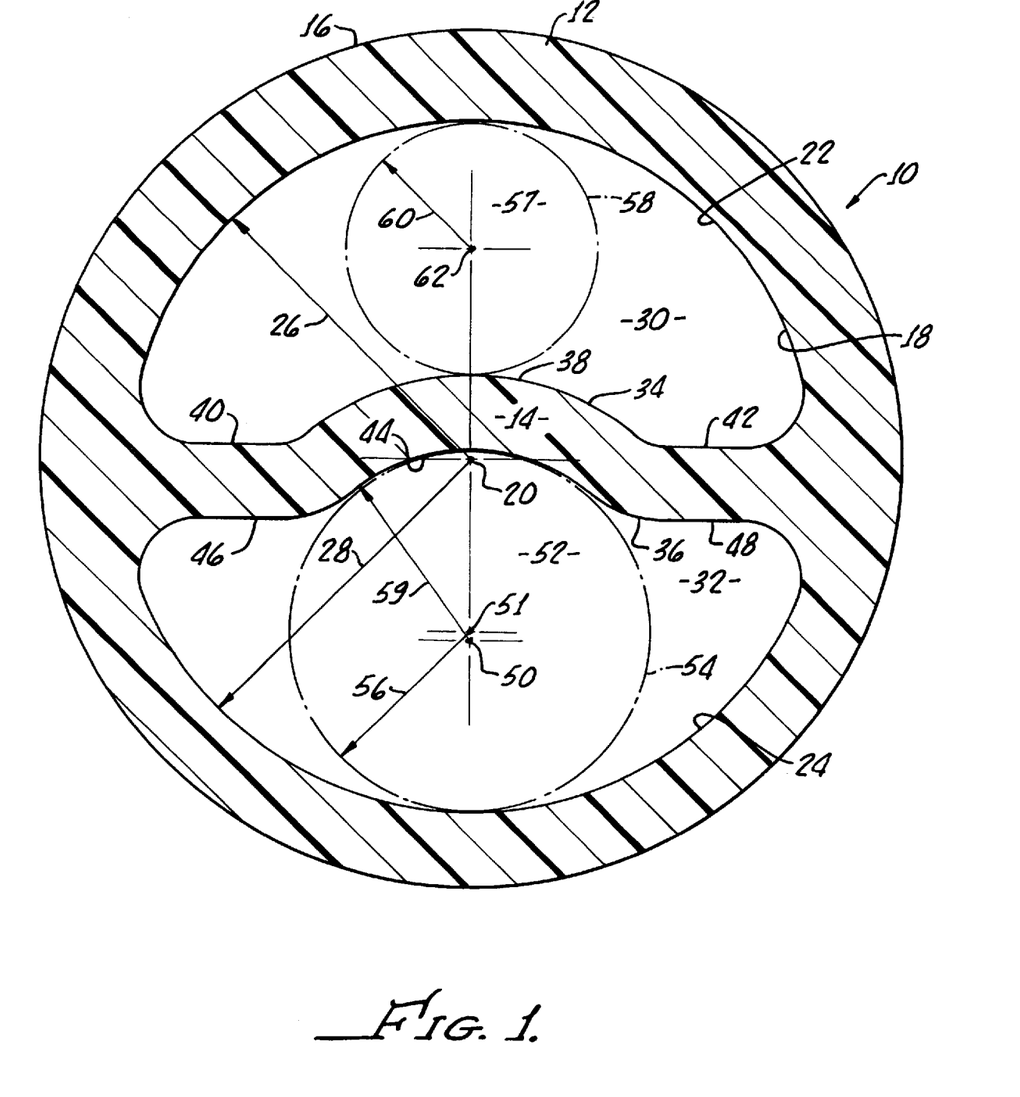
FIG. 1 is a cross-sectional view of a first preferred double lumen tubing in accordance with the present invention.

The lumen wall 14 is connected to the tubular wall 12 and shaped so as to divide the overall tubular conduit into first and second lumens 30 and 32 which have substantially the same cross-sectional areas. In addition, the lumen wall 14 is shaped so as to provide a primary guidewire region which allows passage of a relatively large guidewire through at least one of the lumens. In the preferred embodiment, the lumen wall 14 is shaped to allow passage of a relatively large guidewire through the second lumen 32.

The interior surface 18 is divided into a first lumen portion 22 and a second lumen portion 24. The first lumen portion 22 is located along a first lumen radius measured from the longitudinal central axis 20 as represented by arrow 26. The second lumen portion is located along a second lumen radius measured from the longitudinal central axis as represented by arrow 28. As a feature of the present invention, the first lumen portion radius 26 is less than the second lumen radius 28 to provide a tubular wall 12 which has varying thicknesses. Specifically, the thickness of tubular wall 12 adjacent to the first lumen 30 is slightly greater than the thickness of the tubular wall 12 adjacent to the second lumen 32. This variation in thickness is due to the differences in radiuses 26 and 28. In accordance with the present invention, the strength of tubular wall 12 is increased due to this variation in thicknesses. As can be seen from FIG. 1, the thickness of first lumen portion 22 is greater than the thickness of second lumen portion 24. The slight increase in thickness of tubular wall 12 adjacent to the first lumen portion 22 provides a slight increase in strength of this section of the tubular wall 12, which is unsupported when the second lumen 32 is used as a guidewire passage. The increase in thickness of the tubular wall 12 at the first lumen portion must be kept relatively small so that the preference of substantially equal lumen cross-sections can be maintained. Increases in wall thickness (variations between radii 26 and 28) are preferably in the range of 0.001 to 0.003 inch (0.0254 to 0.0762 mm) for 7 French catheters, for example. A proportional increase in wall thickness within this range should provide a discernible increase in kink resistance.

In order to achieve the above preferences of equal lumen cross-sectional area and large guidewire capabilities, the lumen wall 14 is shaped in the arcuate configuration as shown in FIG. 1. More particularly, the lumen wall 14 has a first surface 34 and a second surface 36. The first surface 34 includes a first lumen central arcuate portion 38 and two first lumen wing portions 40 and 42 located on opposite sides of the first lumen central arcuate portion 38. The second surface 36 of lumen wall 14 also includes a second lumen central arcuate portion 44 and two second lumen wing portions 46 and 48 which are located on opposite sides of the second lumen arcuate portion 44. The first and second lumen central arcuate portions 38 and 44 are in the shape of circular arcs which are concentrically located about an axis 50. In accordance with the present invention, the second lumen central arcuate portion 44 has a radius 59 measured from axis 50 which is equal to 50 to 60 percent of the radius 28 of the second lumen portion interior surface 24. The second lumen central arcuate portion 44, in combination with the second lumen portion 24, defines a circular primary guidewire region 52 which is depicted by the phantom circular line 54 in FIG. 1. The radius of the guidewire region 52 about axis 51 is depicted by arrow 56. It should be noted that the center axis 51 of the circular guidewire region 52 does not fall exactly at the center axis 50 for the lumen wall concentric arcuate portions 38 and 44. The preferred radius 56 for the guidewire region 52 is about 52 percent of the radius 28 for the second lumen portion 24 of interior surface 18.

In addition to accepting guidewires through primary guidewire region 52, the double lumen tubing 10 in accordance with the present invention can also receive guidewires through the first lumen 30. Guidewires passed through lumen 30 must necessarily have a smaller radius than guidewires passed through guidewire region 52. The location through which guidewires may be passed in lumen 30 is shown as secondary guidewire region 57. The circular border of guidewire region 57 is depicted by circular phantom line 58 which has a radius 60 about axis 62. Desirably, in double lumen tubing having substantially equal lumens, the radius of the secondary guidewire region 57 in the first lumen 30 is between about 60 and 70 percent of the radius of the primary guidewire region 52 the second lumen 32.

The double lumen tubing 10 is suitable for use in a wide variety of situations where a dual lumen catheter having two lumens with substantially equal cross-sectional areas are required. The unique shape of multi-curved arcuate lumen wall 14 provides two lumens with substantially equal cross-sectional areas which at the same time also allowing the use of relatively-large guidewires in primary guidewire region 52 and/or relatively small guidewires in secondary guidewire region 57. In addition, the use of a relatively smaller radius for the first lumen portion 22 of interior surface 18 increases the thickness of the tubing wall 12 as discussed above to increase the kink resistance of the tubing 10.

Preferred double lumen tubings are those where the cross-sectional area of the first and second lumens is between 0.0010 and 0.0060 in$^2$ (0.645 and 3.871 mm$^2$). Seven French double lumen tubings having $^{10}$/$_{16}$ gauge individual lumens are preferred. For a seven French double lumen tubing, the cross-sectional areas of the first and second lumens is about 0.0016 in$^2$ (1.032 mm$^2$). Cross-sectional areas of 0.00174 in$^2$ (1.1226 mm$^2$) are also preferred, because this size allows passage of a guidewire of at least 0.035 inch (0.889 mm) diameter along the lumens. Preferably, the radius 28 of the second lumen portion 24 of interior surface 18 is between about 0.035 and 0.040 inch (0.889 and 1.016 mm). It is preferred that the radius 26 of the first lumen portion 22 of interior surface 18 be about 0.001 to 0.003 inch (0.0254 to 0.0762 mm) shorter than the radius 28 of the second lumen portion 24. The cross-sectional area of the second lumen 32 is desirably between 98% and 115% of the area of the first lumen 30, and more preferably the area of the second is within 98% and 100% of the first.

The approximate dimensions for a preferred exemplary double lumen tubing 10 as shown in FIG. 1 are as follows. The radius of the tubular wall exterior surface 16, as measured from longitudinal central axis 20 is 0.0465 inch (1.181 mm). The radius 26 for the first lumen portion 22 of interior surface 18 is 0.0365 inch (0.927 mm). The radius 28 of the second lumen portion 24 of interior surface 18 is 0.0375 inch (0.953 mm). The radius 59 of the second lumen central arcuate portion 44, as measured from axis 51, is 0.0205 inch (0.521 mm). The radius 56 of the primary guidewire region 52, as measured from axis 50, is 0.0195 inch (0.495 mm). The radius of the first lumen central arcuate portion 38 (as measured from axis 50) is 0.0295 inch (0.749 mm).

The lumen walls can be made from any of the conventional materials used in making double lumen catheters. Exemplary materials include polyvinyl chloride (PVC), polyurethane, silicone, polyamids, fluoropolymers (e.g. TEFLON), polyolefins (polyethylene, polypropylene), metalocenes, and thermoplastic elastomers. Polyurethane is the preferred material for use in making double lumen tubings in accordance with the present invention.

Figure 2:
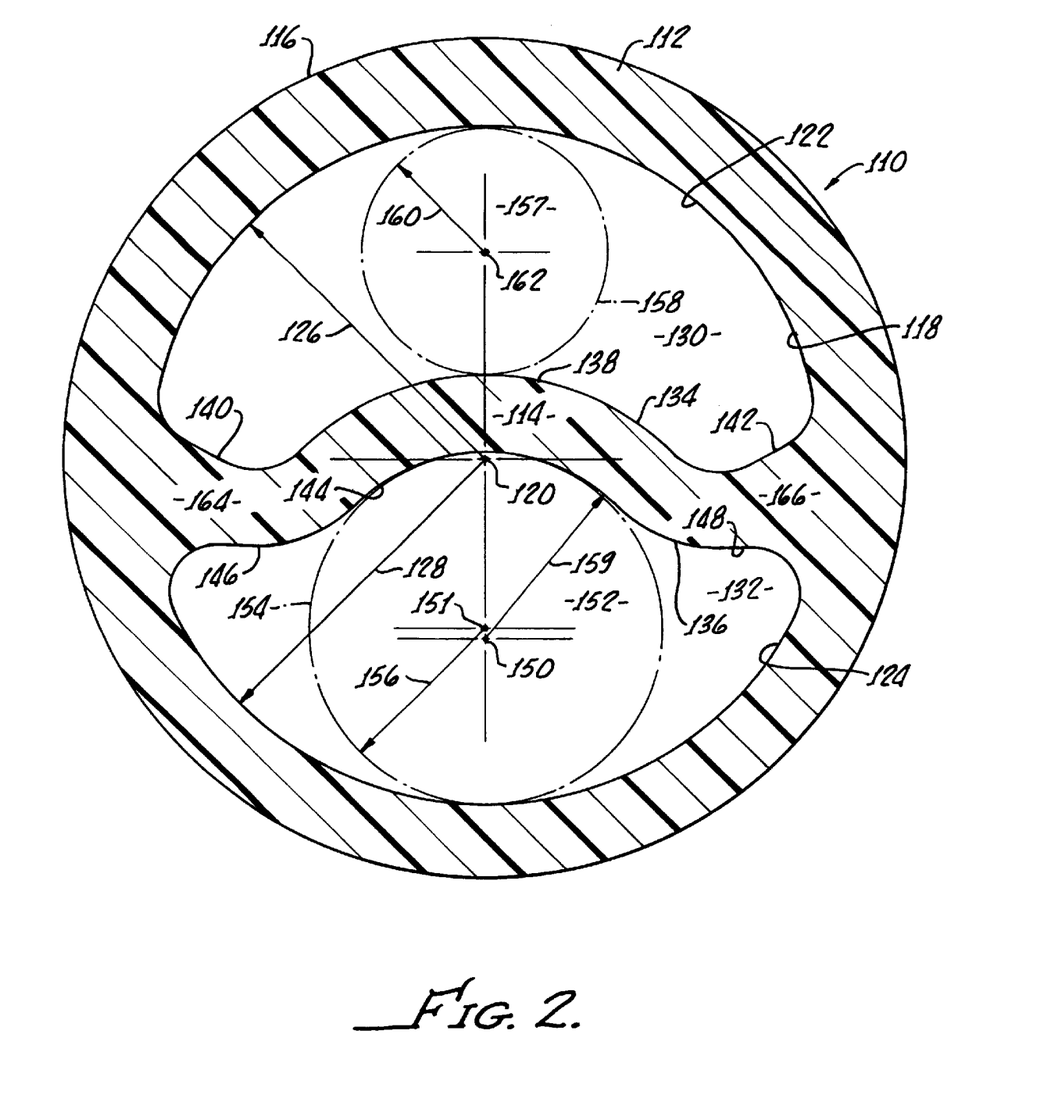
FIG. 2 is a cross-sectional view of a second preferred double lumen tubing in accordance with the present invention.

A second preferred embodiment of the present invention is shown generally at 110 in FIG. 2. The dual lumen tubing 110 is similar to the first tubing embodiment 10 in that both lumens have substantially equal cross-sectional areas and both lumens are capable of receiving a relatively large guidewire through one of the lumens. The principal difference between the two embodiments is that the wing portions of the lumen wall in tubing 110 are shaped differently to provide shoulders which are thicker at their attachment point to the tubular wall.

Referring to FIG. 2, the double lumen tubing 110 includes a tubular wall 112 and a lumen wall 114. The tubular wall 112 has an exterior surface 116 and an interior surface 118. The interior surface 118 has a circular cross-section located about a longitudinal central axis 120. The interior surface 118 defines a tubular conduit across which the lumen wall 114 extends transversely. The lumen wall 114 also extends parallel to the longitudinal central axis 120. In this preferred embodiment, the exterior surface 116 has a circular cross-section which is concentrically located about the interior surface 118.

The lumen wall 114 is connected to the tubular wall 112 and shaped so as to divide the overall tubular conduit into first and second lumens 130 and 132 which have substantially the same cross-sectional areas. In addition, the lumen wall 114 is shaped so as to provide a primary guidewire region which allows passage of a relatively large guidewire through at least one of the lumens. In the preferred embodiment, the lumen wall 114 is shaped to allow passage of a relatively large guidewire through the second lumen 132.

The interior surface 118 is divided into a first lumen portion 122 and a second lumen portion 124. The first lumen portion 122 is located along a first lumen radius measured from the longitudinal central axis 120 as represented by arrow 126. The second lumen portion is located along a second lumen radius measured from the longitudinal central axis as represented by arrow 128. As was the case with the first embodiment, the first lumen portion radius 126 is less than the second lumen radius 128 to provide a tubular wall 112 which has varying thicknesses. Specifically, the thickness of tubular wall 112 adjacent to the first lumen 130 is slightly greater than the thickness of the tubular wall 112 adjacent to the second lumen 132. This variation in thickness is due to the differences in radiuses 126 and 128. In accordance with the present invention, the strength of tubular wall 112 is increased due to this variation in thicknesses. As can be seen from FIG. 2, the thickness of first lumen portion 122 is greater than the thickness of second lumen portion 124. The slight increase in of tubular wall 112 adjacent to the second lumen portion 122 provides a slight increase in strength of this section of the tubular wall, which is unsupported if the second lumen 132 is used exclusively as a guidewire passage.

In order to achieve the above objectives of substantially equal lumen cross-sectional area and large guidewire capabilities, the lumen wall 114 is shaped in the arcuate configuration as shown in FIG. 2. More particularly, the lumen wall 114 has a first surface 134 and a second surface 136. The first surface 134 includes a first lumen central arcuate portion 138 and two first lumen wing portions 140 and 142 located on opposite sides of the first lumen central arcuate portion 138. The second surface 136 of lumen wall 114 also includes a second lumen central arcuate portion 144 and two second lumen wing portions 146 and 148 which are located on opposite sides of the second lumen arcuate portion 144. The first and second lumen central arcuate portions 138 and 144 are in the shape of circular arcs which are concentrically located about a central axis 150. In accordance with the present invention, the second lumen central arcuate portion 144 has a radius 159 measured from axis 150 which is equal to 50 to 60 percent of the radius 128 of the second lumen portion interior surface 124. The second lumen central arcuate portion 144, in combination with second lumen portion 124, defines a circular primary guidewire region 152 which is depicted by the phantom circular line 154 in FIG. 2. The radius 156 of the guidewire region 152, as measured from central axis 151, and by second lumen portion 124, is depicted by arrow 156. The preferred radius 156 for the primary guidewire region 152 is about 52 percent of the radius 128 for the second lumen portion 124 of interior surface 118.

In addition to accepting guidewires through primary guidewire region 152, the double lumen tubing 110 in accordance with the present invention can also receive guidewires through the first lumen 130. Guidewires passed through lumen 130 must necessarily have a smaller radius than guidewires passed through guidewire region 152. The location through which guidewires may be passed in lumen 130 is shown as secondary guidewire region 157. The circular border of guidewire region 157 is depicted by phantom line 158 which has a radius 160 about axis 162.

The double lumen tubing 110 is suitable for use in a wide variety of situations where a dual lumen catheter having two lumens with substantially equal cross-sectional areas are required. The unique shape of multi-curved arcuate lumen wall 114 provides two lumens with substantially equal cross-sectional areas which also allowing the use of relatively-large guidewires in primary guidewire region 152 and/or relatively small guidewires in secondary guidewire region 157. In addition, the use of a relatively smaller radius for the first lumen portion of interior surface 118 increases the thickness of the tubing wall 112 as discussed above to increase the kink resistance of the tubing 110. In addition, the lumen wall 114 is shaped to provide transition shoulders 164 and 166 between the lumen wall 114 and tubular wall 112 which are thicker than the lumen wall 114. These transition shoulders 164 and 166 provide additional reinforcement for tubing 110 which increases the strength and resistance to kinking of the tubing. The approximate dimensions for this second embodiment are the same as those set forth for the first embodiment (FIG. 1).

Figure 3:
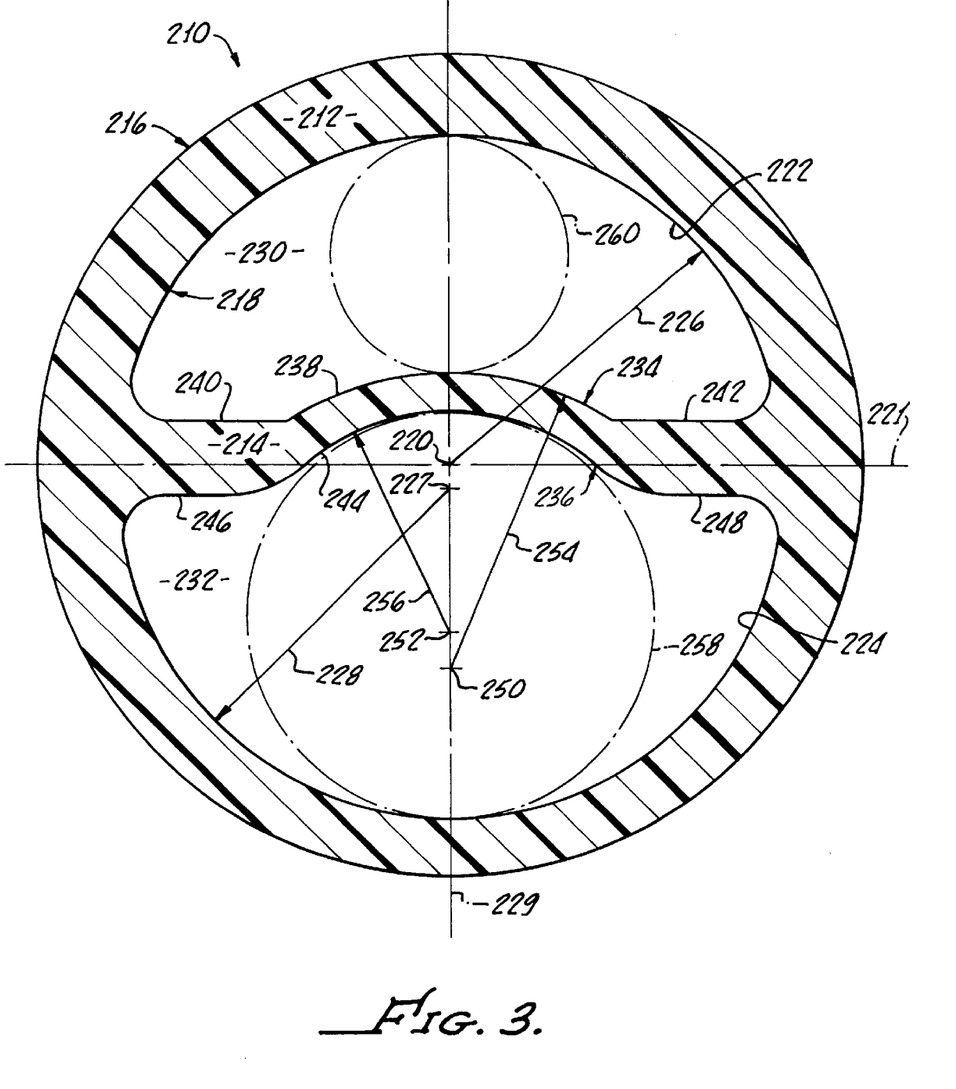
FIG. 3 is a cross-sectional view of a third preferred double lumen tubing in accordance with the present invention.

A third preferred embodiment of the present invention is shown generally at 210 in FIG. 3. The dual lumen tubing 210 is similar to the first and second embodiments in that both lumens are capable of receiving a relatively large guidewire through one of the lumens, and the tubing has increased resistance to kinking. The principal difference in the third embodiment is that the interior surfaces of the two lumens formed thereby have different centers, and the opposite arcuate surfaces of a lumen separating wall are non-concentric as well. Furthermore, the lumen wall is located proximate to or slightly offset from a transverse centerline away from the lumen defining a primary guidewire region so that the lumens are unequal in size yet are both suitable for receiving guidewires or for passing fluid or other instruments.

With reference to FIG. 3, the double lumen tubing 210 includes an outer tubular wall 212 and an inner lumen wall 214. The tubular wall 212 has an exterior surface 216 having a circular cross section located along a longitudinal central axis 220, and an interior surface 218. The interior surface 218 defines a tubular conduit across which the lumen wall 214 extends transversely. The lumen wall 214 also extends longitudinally parallel to the longitudinal central axis 220, and transversely generally along transverse centerline 221. In this embodiment, the exterior surface 216 is concentric about only a portion of the interior surface 218, as explained below.

The interior surface 218 is divided into a first lumen portion 222 and a second lumen portion 224. The first lumen portion 222 is located along a first lumen radius measured from the longitudinal central axis 220 as represented by a radius arrow 226. The second lumen portion 224 is located along a second lumen radius measured from a longitudinal axis 227, as represented by a radius arrow 228. In contrast to the first and second embodiments, the first lumen portion radius 226 is equal to the second lumen portion radius 228. The longitudinal axis 227 is parallel to but offset from the central axis 220 toward the second lumen portion 224, and along transverse centerline 229 perpendicular to transverse centerline 221. Because of this configuration, the tubular wall 212 adjacent to the first lumen portion 222 is slightly greater than the thickness of the tubular wall 212 adjacent to the second lumen portion 224. This variation in thickness is due to the offset axis 227 of the second lumen portion 224, but the thickness variation may alternatively be created by offsetting the axis of the first lumen portion 222. Accordingly, the strength of the tubular wall 212 in the region adjacent the first lumen portion 222 is greater than the strength of the tubular wall adjacent to the second lumen portion 224. This provides increased kink resistance to the tubular wall 212 adjacent the first lumen portion 222, which is unsupported if the second lumen 232 is used exclusively as a guidewire passage.

The lumen wall 214 is connected to the tubular wall 212 and shaped so as to divide the overall tubular conduit into first and second lumens 230 and 232. In addition, the lumen wall 214 is shaped so as to provide a primary guidewire region which allows passage of a relatively large guidewire through at least one of the lumens. In the preferred embodiment, the lumen wall 214 is shaped to allow passage of a relatively large guidewire through the second lumen 232.

In order to accommodate large guidewire capability in one of the lumens, the lumen wall 214 is shaped with an arcuate section as shown in FIG. 3. More particularly, the lumen wall 214 has a first surface 234 and a second surface 236, opposite the first surface. The first surface 234 includes a convex central arcuate portion 238 and two adjacent wing portions 240 and 242. The second surface 236 of lumen wall 214 includes a concave central arcuate portion 244 and two adjacent wing portions 246 and 248.

The convex and concave central arcuate portions 238 and 244 are in the shape of circular arcs non-concentrically located about longitudinal axes 250 and 252, respectively, which are offset along transverse centerline 229. More specifically, the convex arcuate portion 238 is located about a radius 254 centered about longitudinal axis 250, and concave arcuate portion 244 is located about radius 256 centered about longitudinal axis 252. The axis 250 is offset toward the second lumen portion 224 a predetermined distance along the centerline 229 from the axis 252. The length of radius 254 is greater than the length of radius 256 by the distance between the axes 250, 252 plus the thickness of the lumen wall 214 along the centerline 229. The offset between the axes 250, 252 means that the convex arcuate portion 238 has a larger radius of curvature than the concave arcuate portion 244. Thus, the lumen wall 214, in the arcuate central region, is thinnest in the center and gradually thicker toward the adjacent wings. In addition, as seen in FIG. 3, the wings are substantially thicker than any section of the central arcuate portion, which increases the kink resistance of the tubing 210 while maximizing the cross-sectional area of the lumens 230, 232 along the transverse centerline 229. This provides the maximum space for passing large guidewires through the lumens 230, 232.

The concave central arcuate portion 244, in combination with the second lumen portion 224, defines a circular primary guidewire region 258 which is depicted by the phantom circle in the second lumen 232. The guidewire region 258 is centered on or close to the axis 250 of the concave arcuate portion 244. The radius of the guidewire region 258 is preferably slightly less than the radius of the concave arcuate portion 244. To ensure a large area for the primary guidewire region 258, the lumen wall 214 is positioned proximate the transverse centerline 229 and the concave central arcuate portion 244 has a radius which is desirably between approximately 50% and 70% of the radius of the second lumen portion 224. Consequently, the guidewire region 258 has a radius which is also desirably between approximately 50% and 70% of the radius of the second lumen portion 224, though slightly less than the radius of the concave central arcuate portion 244. This preferred ratio is only exemplary, and moderate deviations from the preferred range may still be useful, and serve the purposes of providing a two-lumen tubing with a large guidewire space formed in one, improved kink resistance, and preferably a relatively large space in the other lumen for passing fluids or devices. For example, the fourth embodiment shown in FIG. 4 has a larger second lumen than any of the first three embodiments, and the concave central arcuate portion is offset from the primary guidewire region center with a radius greater than 70% of the radius of the second lumen portion.

In addition to accepting guidewires through primary guidewire region 258, the double lumen tubing 210 in accordance with the present invention can also receive guidewires through the first lumen 230. Guidewires passed through lumen 230 must necessarily have a smaller radius than guidewires passed through small guidewire region 258. The location through which guidewires may be passed in lumen 230 is shown as secondary guidewire region 260, which is depicted by the phantom circle in the first lumen 230. In a preferred embodiment, the secondary guidewire region 258 has a radius which is approximately 40% to 60% of the radius of primary guidewire region 258.

In an exemplary embodiment of the double lumen tubing 210 of FIG. 3, the tubular wall 212 has an OD of 0.100 inch (2.54 mm), the first lumen portion 222 has a radius of 0.040 inch (1.016 mm), the second lumen portion 224 also has a radius of 0.040 inch (1.016 mm), the convex central arcuate portion 238 has a radius of 0.036 inch (0.914 mm), the concave central arcuate portion 244 has a radius of 0.027 inch (0.868 mm), and the axes 250 and 252 are spaced apart by 0.004 inch (0.102 mm). The primary guidewire region 258 has a radius of 0.025 inch (0.635 mm), and the secondary guidewire region 260 has a radius of 0.014 inch (0.336 mm), or about 53% of the primary guidewire region radius. The cross-sectional area of the first lumen 230 is 0.00194 in$^2$ (1.232 mm$^2$), while the cross-sectional area of the second lumen 232 is 0.00278 in$^2$ (1.796 mm$^2$), or about 1.4 times the area of the first lumen.

Figure 4:
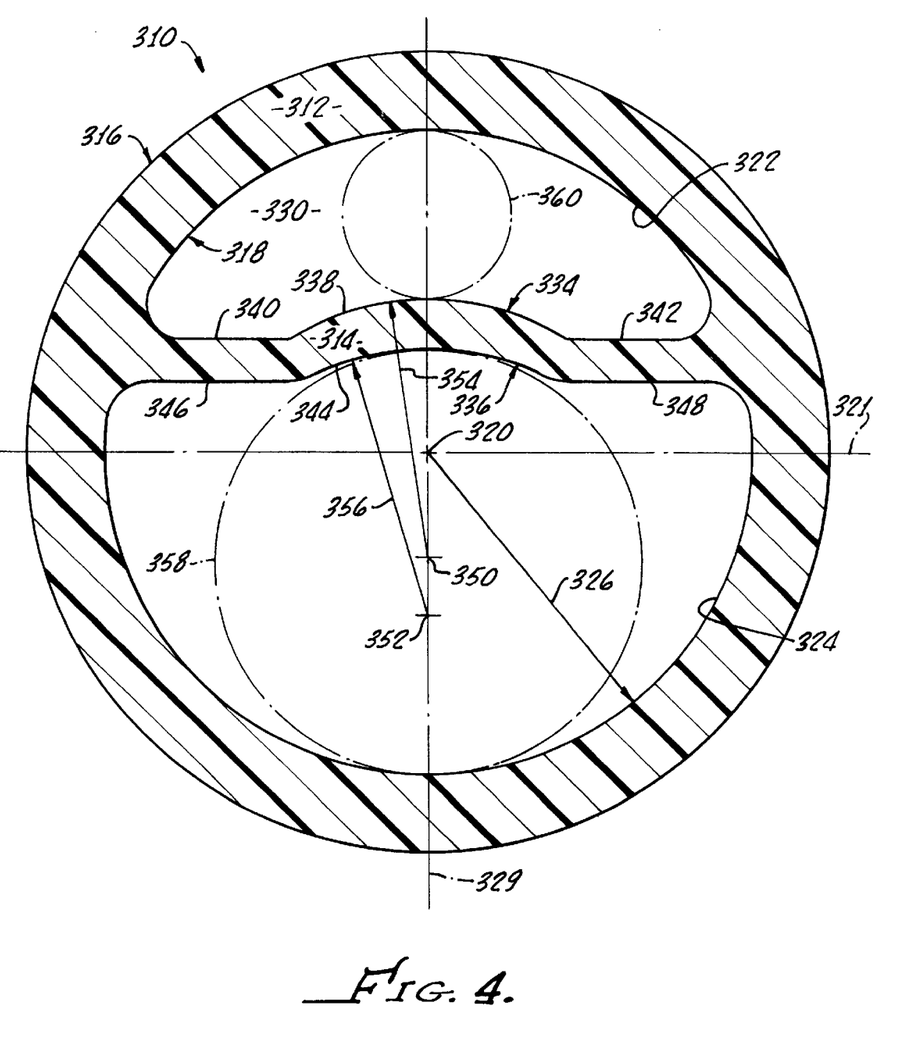
FIG. 4 is a cross-sectional view of a fourth preferred double lumen tubing in accordance with the present invention.

A fourth preferred embodiment of the present invention is shown generally at 310 in FIG. 4. The dual lumen tubing 310 is similar to the first, second and third embodiments in that both lumens are capable of receiving a relatively large guidewire through one of the lumens, and the tubing has increased resistance to kinking. The principal difference in the fourth embodiment is that the opposite arcuate surfaces of a lumen separating wall are non-concentric, and the lumens defined therein have substantially differing cross-sections. Additionally, the lumen wall is offset from a transverse centerline away from the lumen defining a primary guidewire region so that the lumens are unequal in size yet are both suitable for receiving guidewires or for passing fluid or other instruments.

With reference to FIG. 4, the double lumen tubing 310 includes an outer tubular wall 312 and an inner lumen wall 314. The tubular wall 312 has an exterior surface 316 having a circular cross section located along a longitudinal central axis 320, and an interior surface 318. The interior surface 318 defines a tubular conduit across which the lumen wall 314 extends transversely. The lumen wall 314 also extends longitudinally parallel to the longitudinal central axis 320, and transversely generally parallel to transverse centerline 321. In this embodiment, the exterior surface 316 is concentric about the interior surface 318.

The interior surface 318 is divided into a first lumen portion 322 and a second lumen portion 324. The first lumen portion 322 is located along a first lumen radius (not shown) measured from the longitudinal central axis 320. The second lumen portion 324 is located along a second lumen radius measured from measured from the longitudinal central axis 320, as represented by a radius arrow 328. In contrast to the first and second embodiments, the first lumen portion radius is equal to the second lumen portion radius 328.

The lumen wall 314 is connected to the tubular wall 312 and shaped so as to divide the overall tubular conduit into first and second lumens 330 and 332. In addition, the lumen wall 314 is shaped so as to provide a primary guidewire region which allows passage of a relatively large guidewire through at least one of the lumens. In the preferred embodiment, the lumen wall 314 is shaped to allow passage of a relatively large guidewire through the second lumen 332.

In order to accommodate large guidewire capability in one of the lumens, the lumen wall 314 is shaped with an arcuate section as shown in FIG. 4. More particularly, the lumen wall 314 has a first surface 334 and a second surface 336, opposite the first surface. The first surface 334 includes a convex central arcuate portion 338 and two adjacent wing portions 340 and 342. The second surface 336 of lumen wall 314 includes a concave central arcuate portion 344 and two adjacent wing portions 346 and 348.

The convex and concave central arcuate portions 338 and 344 are in the shape of circular arcs non-concentrically located about longitudinal axes 350 and 352, respectively, which are offset along transverse centerline 329 perpendicular to transverse centerline 321. More specifically, the convex arcuate portion 338 is located about a radius 354 centered about longitudinal axis 350, and concave arcuate portion 344 is located about radius 356 centered about longitudinal axis 352. The axis 350 is offset toward the lumen wall 314 a predetermined distance along the centerline 329 from the axis 352. The length of radius 354 is approximately equal to the length of radius 356.

The offset between the axes 350, 352 means that the lumen wall 314 has a thickness in the central arcuate region which is slightly greater in the center than adjacent the wings. In addition, as seen in FIG. 4, the wings are slightly thinner than any section of the central arcuate portion. The thickness of the wings may be manipulated in conjunction with the thickness of the central arcuate region to ensure good kink resistance of the tubing. Thus, if the central portion is constructed relatively thinly, the wings may be increased in size to compensate, and visa versa. Alternatively, the thickness across the entire lumen wall may be relatively constant.

The concave central arcuate portion 344, in combination with the second lumen portion 324, defines a circular primary guidewire region 358 which is depicted by the phantom circle in the second lumen 332. The guidewire region 358 is centered between axes 350 and 352. The radius of the guidewire region 358 is preferably slightly less than the radius of the concave arcuate portion 344. To ensure a large area for the primary guidewire region 358, the lumen wall 314 is offset from the transverse centerline 329 toward the first lumen portion 322 and the concave central arcuate portion 344 has a radius 356 which accommodates a guidewire region 358 radius desirably between approximately 50% and 70% of the radius of the second lumen portion 324. In the embodiment shown, the axis 352 of the concave arcuate portion 344 is offset away from the lumen wall 314, so the radius 356 is necessarily larger than the radius of the guidewire region 358, and conceivably larger than 70% of the radius of the second lumen portion 324.

In addition to accepting guidewires through primary guidewire region 358, the double lumen tubing 310 in accordance with the present invention can also receive guidewires through the first lumen 330. Guidewires passed through lumen 330 must necessarily have a smaller radius than guidewires passed through small guidewire region 358. The location through which guidewires may be passed in lumen 330 is shown as secondary guidewire region 360, which is depicted by the phantom circle in the first lumen 330. In a preferred embodiment, the secondary guidewire region 358 has a radius which is approximately 40% to 60% of the radius of primary guidewire region 358.

In an exemplary embodiment of the double lumen tubing 310 of FIG. 4, the tubular wall 312 has an OD of 0.100 inch (2.54 mm), the first and second lumen portions 322, 324 each has a radius of 0.040 inch (1.016 mm), the convex central arcuate portion 338 has a radius of 0.032 inch (0.813 mm), the concave central arcuate portion 344 has a radius of 0.033 inch (0.838 mm), and the axes 350 and 352 are spaced apart by 0.007 inch (0.178 mm). The primary guidewire region 358 has a radius of 0.027 inch (0.686 mm), and the secondary guidewire region 360 has a radius of 0.011 inch (0.279 mm), or about 40% of the primary guidewire region radius. The cross-sectional area of the first lumen 330 is 0.00131 in$^2$ (0.843 mm$^2$), while the cross-sectional area of the second lumen 332 is 0.00332 in$^2$ (2.141 mm$^2$), or about 2.5 times (254%) the area of the first lumen.

The double lumens in accordance with the present invention utilize in an optimized fashion the available area of the tubular cross-section of the overall lumen to provide maximum lumen areas for flow, and the required walls to provide a structure that is sufficiently kink resistant, without wasting any additional area. This double lumen configuration provides the maximum possible flow rates for the two lumens with a minimum risk that the tube will kink and restrict the flow of fluid.

Having thus described exemplary embodiments of the present invention, it should be noted by those skilled in the art that the disclosures herein are exemplary only and that various other alternations, adaptations and modifications may be made within the scope of the present invention. Accordingly, the present invention is not limited to the specific embodiments as illustrated herein.

What is claimed is:

1. A double lumen tubing adapted for use as a catheter, the double lumen tubing comprising:

a tubular wall having an exterior surface located about a longitudinal central axis and an interior surface, the interior surface cross-section being defined by a circular first lumen portion located along a first lumen radius about a first longitudinal axis and a circular second lumen portion located along a second lumen radius about a second longitudinal axis; and a lumen wall extending longitudinally parallel to the central axis and extending transversely across the tubular conduit between spaced locations on the interior surface, the lumen wall comprising a central arcuate portion and having a first surface which, with the first lumen portion of the interior surface, borders a first lumen, the first lumen having a cross-sectional area, the lumen wall further comprising a second surface opposite the first surface which, with the second lumen portion of the interior surface, borders a second lumen, the second lumen having a cross-sectional area, the first surface of the lumen wall having a central convex arcuate portion and adjacent wing portions extending in opposite directions to the tubular wall, the second surface of the lumen wall having a central concave arcuate portion and adjacent wing portions extending in opposite directions to the tubular wall, wherein the concave arcuate portion is in the shape of a circular arc which has a radius that is from 50 to 90 percent of the radius of the second lumen portion of the interior surface, and wherein a circular primary guidewire region is formed in the second lumen bordered on one side by the concave arcuate portion and on the other side by the second lumen portion, the primary guidewire region having a radius of from 50 to 70 percent of the radius of the second lumen portion.

2. A double lumen tubing according to claim 1 wherein the exterior surface has a circular cross-section concentrically located about the interior surface and wherein the radius of the first lumen portion is less than the radius of the second lumen portion to thereby provide a tubular wall having varying thicknesses wherein the thickness of the tubular wall adjacent to the first lumen is greater than the thickness of the tubular wall adjacent to the second lumen.

3. A double lumen tubing according to claim 1 wherein the exterior surface has a circular cross-section non-concentrically located about a portion of the interior surface to thereby provide a tubular wall having varying thicknesses wherein the thickness of the tubular wall adjacent to the first lumen is greater than the thickness of the tubular wall adjacent to the second lumen.

4. A double lumen tubing according to claim 3 wherein the central axis is coincident with the first longitudinal axis and the second longitudinal axis is offset therefrom and toward the second lumen portion.

5. A double lumen tubing according to claim 1 wherein the concave arcuate portion is situated with respect to the second lumen portion of the interior surface so that the primary guidewire region has a radius of between about 50 and 60 percent of the radius of the second lumen portion.

6. A double lumen tubing according to claim 5 wherein the concave arcuate portion is in the shape of a circular arc having a radius between about 50 and 60 percent of the radius of the second lumen portion.

7. A double lumen tubing according to claim 1 wherein the concave arcuate portion is non-concentric about the primary guidewire region.

8. A double lumen tubing according to claim 1 wherein the concave arcuate portion and convex arcuate portion of the lumen wall are shaped so that the central arcuate portion of the lumen wall has a varying thickness.

9. A double lumen tubing according to claim 8 wherein the concave arcuate portion is non-concentric with respect to the convex arcuate portion.

10. A double lumen tubing according to claim 8 wherein the central arcuate portion is thickest in the middle.

11. A double lumen tubing according to claim 8 wherein the central arcuate portion is thinnest in the middle.

12. A double lumen tubing according to claim 1 wherein the wing portions of the opposed first and second surfaces of the lumen wall diverge as they approach the tubular wall interior surface to provide additional kink resistance to the double lumen tubing.

13. A double lumen tubing according to claim 1 wherein the wing portions of the opposed first and second surfaces of the lumen wall are greater in thickness than the thickness of the central arcuate portion to provide additional kink resistance to the double lumen tubing.

14. A double lumen tubing according to claim 1 wherein the concave arcuate portion has a larger radius than the primary guidewire region.

15. A double lumen tubing according to claim 1 wherein the cross-sectional area of the second lumen is between about 98% to about 254% of the cross-sectional area of the first lumen.

16. A double lumen tubing according to claim 15 wherein a circular secondary guidewire region is formed in the first lumen bordered by the convex arcuate portion and the first lumen portion which has a radius of from 40 to 60 percent of the radius of the primary guidewire region.

17. A double lumen tubing according to claim 15 wherein the cross-sectional area of the second lumen is substantially equal to the cross-sectional area of the first lumen.

18. A double lumen tubing according to claim 17 wherein the cross-sectional area of the second lumen is between about 98% to about 115% of the cross-sectional area of the first lumen.

19. A double lumen tubing according to claim 17 wherein a circular secondary guidewire region is formed in the first lumen bordered by the convex arcuate portion and the first lumen portion which has a radius of from 60 to 70 percent of the radius of the primary guidewire region.

20. A guidewire introduction system comprising a double lumen tubing according to claim 19 and a guidewire located within the secondary guidewire region.

21. A guidewire introduction system comprising a double lumen tubing according to claim 1 and a guidewire located within the primary guidewire region.

* * * * *